(12) United States Patent
Hara et al.

(10) Patent No.: US 8,445,213 B2
(45) Date of Patent: May 21, 2013

(54) PURIFIED SERUM ALBUMIN, AND IMMUNOLOGICAL MEASUREMENT METHOD

(75) Inventors: Yasuyuki Hara, Ibaraki (JP); Takayuki Akamine, Osaka (JP); Katsumi Yoshikawa, Tokyo (JP); Michiko Kawamoto, Ibaraki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 31 days.

(21) Appl. No.: 12/935,368

(22) PCT Filed: Mar. 27, 2009

(86) PCT No.: PCT/JP2009/056316
§ 371 (c)(1),
(2), (4) Date: Sep. 29, 2010

(87) PCT Pub. No.: WO2009/123060
PCT Pub. Date: Oct. 8, 2009

(65) Prior Publication Data
US 2011/0027912 A1   Feb. 3, 2011

(30) Foreign Application Priority Data
Mar. 31, 2008   (JP) .................................. 2008-093001

(51) Int. Cl.
*G01N 33/53*   (2006.01)

(52) U.S. Cl.
USPC ........................................... 435/7.1; 436/518

(58) Field of Classification Search ........................ None
See application file for complete search history.

(56) References Cited

U.S. PATENT DOCUMENTS

| 5,506,110 A | 4/1996 | Matsuura et al. |
| 6,150,504 A | 11/2000 | Van Der Laken et al. |
| 2003/0204060 A1 | 10/2003 | Van Der Laken et al. |

FOREIGN PATENT DOCUMENTS

| CN | 1191545 | 8/1998 |
| CN | 1235981 | 11/1999 |
| CN | 1339065 | 3/2002 |
| CN | 1496993 | 5/2004 |
| CN | 1525977 | 9/2004 |
| CN | 1628129 | 6/2005 |
| JP | 4-122858 | 4/1992 |
| JP | 10-197530 | 7/1998 |
| JP | 2000-046828 | 2/2000 |
| WO | WO-9637515 | * 11/1996 |
| WO | 03/097693 | 11/2003 |

OTHER PUBLICATIONS

Cabrera-Crespo et al. (Biotech Appl Biochem 2000 vol. 31, p. 101-106).*
Supplementary European Search Report issued Mar. 22, 2011 in European Application No. 09728817.9.
S. J. Frost et al., "A Novel Colourimetric Homogeneous Liposomal Immunoassay using Sulphorhodamine B", Journal of Liposome Research, vol. 4, No. 3, pp. 1159-1182, Nov. 1, 1994.

* cited by examiner

*Primary Examiner* — Jacob Cheu
(74) *Attorney, Agent, or Firm* — Wenderoth, Lind & Ponack, L.L.P.

(57) ABSTRACT

An object of the present invention is to provide: a purified serum albumin having less lot-to-lot variation; and an immunoassay method utilizing the purified serum albumin, in which high reactivity and less non-specific reactions are achieved.

The present invention provides a purified serum albumin, which is a serum albumin used as a blocking agent and/or in a suspension containing an insoluble carrier in an immunoassay method, and is composed mostly of a fraction, the fraction having an absorbance of not exceeding 9.0 mAbs when measured in the form of 1% aqueous solution at a wavelength of 463 nm by using a quarts cell having an optical path length of 1.0 cm.

9 Claims, 1 Drawing Sheet

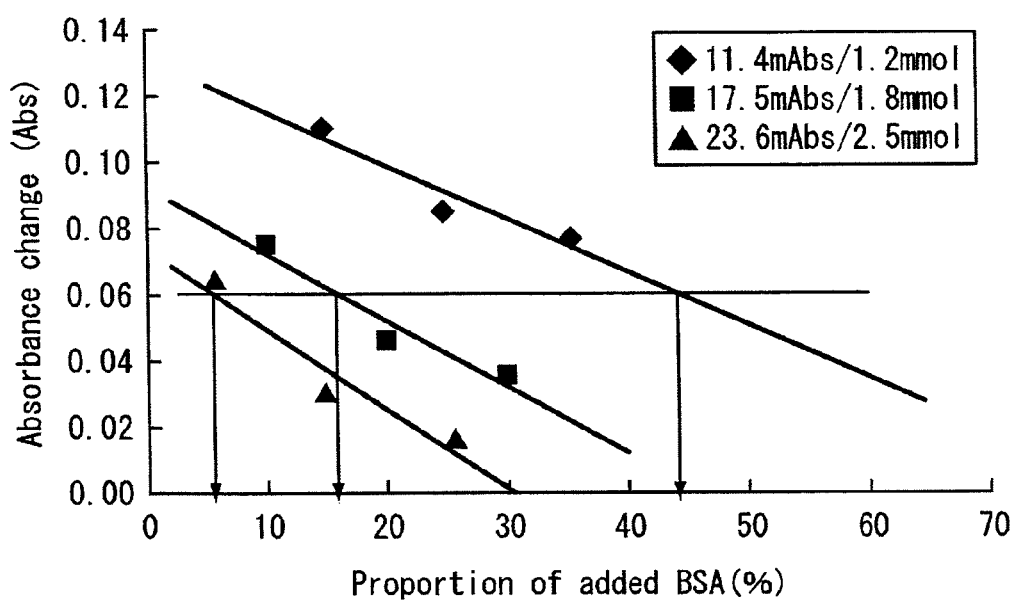

PURIFIED SERUM ALBUMIN, AND IMMUNOLOGICAL MEASUREMENT METHOD

This application is a U.S. national stage of International Application No. PCT/JP2009/056316 filed Mar. 27, 2009.

TECHNICAL FIELD

The present invention relates to: a purified serum albumin having less lot-to-lot variation; and an immunoassay method carried out with use of the purified serum albumin, in which high reactivity and less non-specific reactions are achieved.

BACKGROUND ART

An immunoassay method is employed for measuring trace substances contained in blood, urine, and the like. Since the immunoassay method is based on a strong specific antigen-antibody binding, specific and high-sensitivity measurement of the objective substance is possible even from a sample containing various substances therein.

However, there has been a growing need for measurement of ultra-trace substances including: a cancer marker in the blood, antigens such as a virus; and antibodies against bacteria and viruses. As a result, a higher-sensitivity measurement has been strongly desired in the immunoassay method.

Conventionally-disclosed methods for achieving the higher-sensitivity measurement in the immunoassay method include a method of adding a reaction accelerator to a reagent (Patent Document 1), a method of adding a large amount of inactive protein to a reaction system (Patent Document 2), and a method of heat-denaturing a blocking agent when conducting blocking of antigens and antibodies immobilized on insoluble carriers with immunoinactive proteins (Patent Document 3).

However, the method of adding a reaction accelerator disclosed in Patent Document 1 has a problem that a non-specific reaction may be induced.

In the methods disclosed in Patent Documents 2 and 3, serum-derived albumin is commonly used as a blocking agent for preventing a non-specific reaction. However, serum albumin products have problems that the reactivity may vary widely from lot to lot and that a sufficient effect may not be obtained.

Patent Document 1: Japanese Kokai Publication H04-122858 (JP-A H04-122858)
Patent Document 2: Japanese Kokai Publication 2000-46828 (JP-A 2000-46828)
Patent Document 3: Japanese Kokai Publication H10-197530 (JP-A H10-197530)

SUMMARY OF THE INVENTION

Problems to be Solved by the Invention

In view of the above state of the art, an object of the present invention is to provide: a purified serum albumin having less lot-to-lot variation; and an immunoassay method carried out with use of the purified serum albumin, in which high reactivity and less non-specific reactions are achieved.

Means for Solving the Problems

The present invention 1 is a purified serum albumin, which is a serum albumin used as a blocking agent and/or in a suspension containing an insoluble carrier in an immunoassay method, and is composed mostly of a fraction, the fraction having an absorbance of not exceeding 9.0 mAbs when measured in the form of 1% aqueous solution at a wavelength of 463 nm by using a quarts cell having an optical path length of 1.0 cm.

The present invention 2 is a purified serum albumin, which is used as a blocking agent and/or in a suspension containing an insoluble carrier in an immunoassay method, and is composed mostly of a fraction, the fraction having bilirubin binding capacity of not exceeding 0.9 mmol with respect to 1 mol of serum albumin.

The present invention is specifically described in the following.

As a result of the intensive study, the present inventors found the following. It is possible to carry out an immunoassay in which minimal influence of lot-to-lot variation of purified serum albumin, high reactivity, and less non-specific reactions are achieved, in the case where a purified serum albumin is used as a blocking agent and/or in a suspension containing an insoluble carrier, the purified serum albumin comprising a fraction having: an absorbance of not exceeding 9.0 mAbs when measured in the form of 1% aqueous solution at a wavelength of 463 nm by using a quarts cell having an optical path length of 1.0 cm; or bilirubin binding capacity of not exceeding 0.9 mmol with respect to 1 mol of serum albumin. Accordingly, the present inventors completed the present invention.

The reason has not been clarified yet. Here, serum albumin in blood is adsorbing bilirubin (yellow pigment component), free fatty acids and the like to transfer them. The lot-to-lot variation of the conventional serum albumin products is presumably caused by the presence of the adsorbate and the amount difference thereof. Since the fractions satisfying the requirements of the present inventions 1 and 2 have minimal adsorbate, a purified serum albumin composed mostly of the fractions presumably enables an immunoassay in which high reactivity and less non-specific reactions are achieved.

The purified serum albumin of the present invention 1 is composed mostly of a fraction having an absorbance of not exceeding 9.0 mAbs when measured in the form of 1% aqueous solution at a wavelength of 463 nm by using a quarts cell having an optical path length of 1.0 cm. Preferably, the purified serum albumin is composed mostly of a fraction having an absorbance of not exceeding 8.0 mAbs when measured in the form of 1% aqueous solution at a wavelength of 463 nm by using a quarts cell having an optical path length of 1.0 cm. More preferably, the purified serum albumin is composed mostly of a fraction having an absorbance of not exceeding 7.0 mAbs when measured in the form of 1% aqueous solution at a wavelength of 463 nm by using a quarts cell having an optical path length of 1.0 cm.

Such fractions of the serum albumin minimally adsorb bilirubin (yellow pigment component, absorption wavelength of 438 nm (BSA-bound bilirubin: 463 nm)) and the like. Therefore, when the purified serum albumin of the present invention which is mostly composed of such a fraction is used as a blocking agent and/or in a suspension containing an insoluble carrier, it is possible to carry out an immunoassay in which minimal influence of lot-to-lot variation of the purified serum albumin, high reactivity, and less non-specific reactions are achieved.

It is to be noted that "composed mostly of" preferably refers to "composed only of the above-mentioned fraction", but may refer to "composed of the above-mentioned fraction and other fractions in a ratio that does not interfere the aimed effect of the present invention".

The acceptable amount of the other fractions is different in accordance with the kind thereof. The amount ratio that allows the absorbance change of not less than 0.06 Abs at 127 T.U. and at a wavelength of 700 nm was calculated based on Table 5 and FIG. 1.

For example, in the case where a fraction has an absorbance in the range of 9.0 to 13.5 mAbs (not including 9.0 and including 13.5) when measured in the form of 1% aqueous solution at a wavelength of 463 nm by using a quarts cell having an optical path length of 1.0 cm, up to about 45% by weight of such a fraction may be mixed in the serum albumin.

For another example, in the case where a fraction has an absorbance in the range of 9.0 to 20.0 mAbs (not including 9.0 and including 20.0) when measured in the form of 1% aqueous solution at a wavelength of 463 nm by using a quarts cell having an optical path length of 1.0 cm, up to about 15% by weight of such fractions may be mixed in the serum albumin.

For still another example, in the case where a fraction has an absorbance in the range of 9.0 to 26.0 mAbs (not including 9.0 and including 26.0) when measured in the form of 1% aqueous solution at a wavelength of 463 nm by using a quarts cell having an optical path length of 1.0 cm, up to about 5% by weight of such fractions may be mixed in the serum albumin.

Here, "T.U." in the present description is an abbreviation of TITER UNITS that is a unit of the anti-treponemal antibody titer measured with use of Mediace TPLA (manufactured by SEKISUI MEDICAL CO., LTD.) which is a kit for measuring the treponemal antibody. If a WHO international standard (THE INTERNATIONAL STANDARD for SYPHILITIC HUMAN SERUM [$1^{st}$ international standard preparation], established in 1958) is measured by using this, 1 T.U. corresponds to 2 mIU. In addition, the value of 10 T.U. or higher is regarded as a positive result.

The purified serum albumin of the present invention 2 is composed mostly of a fraction having bilirubin binding capacity of not exceeding 0.9 mmol with respect to 1 mol of serum albumin. Preferably, the purified serum albumin is mostly composed of a fraction having bilirubin binding capacity not exceeding 0.8 mmol with respect to 1 mol of serum albumin. More preferably, the purified serum albumin is mostly composed of a fraction having bilirubin binding capacity not exceeding 0.7 mmol with respect to 1 mol of serum albumin. When the purified serum albumin of the present invention which is mostly composed of such a fraction is used as a blocking agent and/or in a suspension containing an insoluble carrier, it is possible to carry out an immunoassay in which minimal influence of lot-to-lot variation of the purified serum albumin, high reactivity, and less non-specific reactions are achieved.

It is to be noted that "composed mostly of" preferably refers to "composed only of the above-mentioned fraction", but may refer to "composed of the above-mentioned fraction and other fractions in a ratio that does not interfere the aimed effect of the present invention".

The bilirubin binding capacity with respect to 1 mol of serum albumin is measured, for example, with use of a reagent for measuring bilirubin ("Autosera BIL-2", "Autosera D-BIL-2" manufactured by SEKISUI MEDICAL CO., LTD.) by an azobilirubin method.

The acceptable amount of the other fractions is different in accordance with the kind thereof. The amount ratio that allows the absorbance change of not less than 0.06 Abs at 127 T.U. and at a wavelength of 700 nm was calculated based on Table 5 and FIG. 1.

For example, in the case where a fraction has bilirubin binding capacity of 0.9 to 1.5 mmol (not including 0.9 and including 1.5) with respect to 1 mol of serum albumin therein, up to about 45% by weight of such fractions may be mixed in the serum albumin.

For another example, in the case where a fraction has bilirubin binding capacity of 0.9 to 2.0 mmol (not including 0.9 and including 2.0) with respect to 1 mol of serum albumin therein, up to about 15% by weight of such fractions may be mixed in the serum albumin.

For still another example, in the case where a fraction has bilirubin binding capacity of 0.9 to 2.7 mmol (not including 0.9 and including 2.7) with respect to 1 mol of serum albumin therein, up to about 5% by weight of such fractions may be mixed in the serum albumin.

The fraction having: an absorbance of not exceeding 9.0 mAbs when measured in the form of 1% aqueous solution at a wavelength of 463 nm by using a quarts cell having an optical path length of 1.0 cm; or bilirubin binding capacity of not exceeding 0.9 mmol with respect to 1 mol of serum albumin can be obtained, for example, by elution with use of an eluent containing a salt at a concentration of not exceeding 150 mM in anion-exchange chromatographic purification.

Serum albumin material used for preparing the purified serum albumin of the present invention is derived from animal serum. Specifically, the serum albumin material is preferably derived from the serum of large mammals such as human, bovine, horse, and sheep. Among these, serum albumin material derived from bovine is particularly preferable because it is available in large quantities at low cost.

The serum albumin material is preferably partially purified by Cohn method, heat-shock method and the like, prior to the anion-exchange chromatographic purification.

A carrier in the column used in the anion-exchange chromatographic purification is not particularly limited, and examples thereof include DEAE Sepharose Fast Flow and ANX Sepharose 4Fast Flow which are weak anionic and Q sepharose Fast Flow and Q sepharose XL which are strong anionic.

The preferable lower limit of the particle size of the carrier in the column used in the anion-exchange chromatographic purification is 10 µm and the preferable upper limit thereof is 200 µm. The carrier having a particle size smaller than 10 µm may increase the back pressure to cause a case where the flow rate of the serum albumin at purification needs to be lowered. In contrast, the carrier having a particle size larger than 200 µm may decrease the separation capacity of the column. The more preferable lower limit of the particle size of the carrier in the column is 45 µm and the more preferable upper limit thereof is 165 µm.

The column used in the anion-exchange chromatographic purification may be a commercially available product such as HiPrep16/10DEAE FF, HiPrep16/10ANX FF (high sub), and HiPrep16/10Q FF (all manufactured by GE Healthcare Inc.).

A buffer solution (hereinafter, also referred to as coupling liquid) used for coupling serum albumin with the carrier in the column in anion-exchange chromatographic purification is not particularly limited, and examples thereof include phosphate buffer solution, glycine buffer solution, and tris buffer solution.

The concentration of the buffer solution is commonly in the range from 5 to 150 mM.

The buffer solution preferably has a pH in the range from 4 to 9, more preferably in the range from 5 to 8.

The eluent used in the anion-exchange chromatographic purification may contain a salt at a concentration of not exceeding 150 mM, and examples thereof include a buffer solution, such as phosphate buffer solution, glycine buffer solution, and tris buffer solution, added with the salt at a concentration of not exceeding 150 mM.

The salt is not particularly limited and examples thereof include sodium chloride (NaCl) and potassium chloride (KCl).

The eluent preferably has a pH in the range from 4 to 9, more preferably in the range from 5 to 8.

Here, the same buffer solution as the coupling liquid added with salt is commonly used.

A preferable example of the anion-exchange chromatographic purification is described in the following.

First, a solution containing a coupling liquid (e.g. 50 mM Tris-HCl buffer solution (pH 7.5)) added with serum albumin is prepared.

Next, the solution is added to an anion-exchange column equilibrated by the coupling liquid, and the coupling liquid is flowed so that the anion-exchange column adsorbs the serum albumin.

Then, the eluent containing the salt at a concentration of not exceeding 150 mM is flowed so that serum albumin is eluted. In this manner, the purified serum albumin is obtained.

The purified serum albumin obtained by the anion-exchange chromatographic purification may be further purified by dialysis or gel filtration.

The purified serum albumin of the present invention has minimal lot-to-lot variation.

Use of the purified serum albumin of the present invention as a blocking agent or in a suspension containing an insoluble carrier enables an immunoassay in which high reactivity and less non-specific reactions are achieved.

The present invention also provides an immunoassay reagent comprising the purified serum albumin of the present invention.

The present invention also provides an immunoassay method which is carried out by utilizing an antigen-antibody reaction with use of the purified serum albumin of the present invention as a blocking agent and/or in a suspension containing an insoluble carrier.

The present invention also provides a reagent for preparation of solid-phase used in immunoassay, which is composed mostly of the purified serum albumin of the present invention.

A monomer obtainable by purifying the purified serum albumin of the present invention by gel filtration is used for further improving the reactivity of the immunoassay reagent.

The immunoassay method of the present invention is described in more detail.

Examples of a measuring object in the immunoassay method of the present invention include an antigen or antibody in a biological material. Specific examples thereof include antigens derived from hepatitis (B and C) and antibodies thereto, HIV antigens and antibodies thereto, antibodies derived from syphilis, cancer markers such as α-fetoprotein, hormones such as insulin, and autacoids.

Particularly, the immunoassay method can effectively detect anti-treponema pallidum antibodies that are antibodies derived from syphilis among these.

Broken cells or a purified product of antigens may be used in a system for assaying the anti-treponema pallidum antibodies. In addition, artificially synthesized antigens may be used singly or in combination of two or more species of them.

The immunoassay method of the present invention is not particularly limited. However, a method in which antigens or antibodies are supported on an insoluble carrier is preferable.

The insoluble carrier is not particularly limited, and examples thereof include organic polymer powder, microorganisms, blood cells, and cell membrane fractions. Among these, organic polymer powder is preferable.

The organic polymer powder is not particularly limited and examples thereof include natural polymer powder, and synthetic polymer powder.

The natural polymer powder is not particularly limited and examples thereof include insoluble agarose, cellulose, and insoluble dextran.

The synthetic polymer powder is not particularly limited and examples thereof include polystyrene, styrene-sulfonate copolymer, styrene-methacrylic acid copolymer, acrylonitrile-butadiene-styrene copolymer, polyvinyl chloride-acrylate copolymer, and vinyl acetate acrylate copolymer.

Further, a sulfonate group, a carboxyl group or the like may be introduced onto the surface of the insoluble carrier.

Latex particles obtainable by uniformly suspending synthetic polymer powder are particularly preferable as the insoluble carrier.

The particle size of the latex particles is not particularly limited. However, the preferable lower limit is 0.05 μm and the preferable upper limit is 1.5 μm. When the particle size of the latex particles is smaller than 0.05 μm, high sensitivity required for the assay may not be achieved because the optical change by the agglutination of the latex particles is small. In contrast, when the particle size thereof is larger than 1.5 μm, the measuring range may be narrowed because the optical change by the agglutination of the latex particles exceeds the measurable level. The particle size of the latex particles more preferably has the lower limit of 0.1 μm and the upper limit of 0.8 μm.

A method for supporting antigens or antibodies on an insoluble carrier is not particularly limited, and a conventionally known method may be employed in which antigens or antibodies are physically or chemically bound to be supported on an insoluble carrier.

In the immunoassay method of the present invention, the purified serum albumin of the present invention is used as a blocking agent for the insoluble carrier (latex particles) having antigens or antibodies supported thereon, or in a suspension of the insoluble carrier having antigens or antibodies supported thereon.

A sample is added to the thus obtained suspension of latex particles having antigens or antibodies supported thereon, and components are reacted for a predetermined time. After that, the degree of agglutination caused by the reaction between the antigens or antibodies supported on the latex particles and a measuring object is optically measured or visually observed. In such manner, the measuring object in the sample is measured.

A method for optically measuring the degree of agglutination is not particularly limited. Fluctuations in scattered light intensity, absorbance of light, light transmission and the like are measured by changing the particle size of the insoluble carrier to be used, concentration, and reaction time. In addition, these may be used in combination.

The wavelength of the light is preferably 300 to 900 nm in conducting the above measurement.

Examples of a device used for the above optical measurement include an optical instrument for detecting scattered light intensity, absorbance of light, light transmission, and the like, and any of commonly-available biochemical autoanalyzers may be used.

Examples of a method for visually observing the degree of agglutination include a conventional method comprising the steps of: preparing a solution containing a sample and a suspension of latex particles by mixing them on a determination plate; moving the prepared solution; and determining the presence of agglutination. Here, in addition to the visual observation, the degree of agglutination may be observed by filming the agglutination state by using a video camera and the like and processing the filmed image.

Effects of the Invention

According to the present invention, it is possible to provide a purified serum albumin having less lot-to-lot variation; and an immunoassay method carried out with use of the purified serum albumin, in which high reactivity and less non-specific reactions are achieved.

BEST MODES FOR CARRYING OUT THE INVENTION

Embodiments of the present invention are described in more detail with reference to Examples. However, the present invention is not limited only to these examples.

Example 1

(1) Preparation of Purified Serum Albumin

A commercially-available bovine serum albumin (manufactured by Serologicals Corporation, "Cohn Fraction V", hereinafter, also referred to as "crude BSA", Lot 83) was added to a coupling liquid (50 mM Tris-HCl buffer solution (pH 7.5)) to produce 15% crude BSA solution.

An amount of 5 mL of the obtained 15% crude BSA solution was added to a commercially-available anion-exchange column (manufactured by GE Healthcare Inc., 480 mL of "DEAE SepharoseFF"/"XK50") equilibrated by the coupling liquid in advance. The coupling liquid was flowed at the rate of 4 mL/min so that the column adsorbs the BSA. Then, an eluent having a sodium chloride concentration of 80 mM was flowed at the rate of 10 mL/min so that an albumin fraction was eluted. Here, the eluent having a sodium chloride concentration of 80 mM was prepared by blending a 2 M sodium chloride solution with the coupling liquid. Separately, as a 2 M sodium chloride solution was mixed with the coupling agent in such a manner that the sodium chloride concentration was increased at the rate of 2 mM/min, the mixed solution of the 2 M sodium chloride solution and the coupling agent was flowed at the rate of 10 mL/min. In this manner, an albumin fraction was eluted within 73.3 to 74.5 minutes after commencement of mixing (fractions having a salt concentration of 69.6 to 72.0 mM). Here, the salt concentration of the obtained albumin fractions is the sodium chloride concentration of the albumin solution eluted from the column determined in consideration of the volume of the column.

The obtained fraction solutions were respectively dialyzed against 100 mM phosphate buffer solution (pH 7.4) so as to produce 1% solutions thereof. The absorbance of light of the obtained 1% solutions of purified serum albumin was measured at a wavelength of 463 nm with use of a standard cell (manufactured by GL Sciences Inc., "S10-UV", optical path length of 1.0 cm). The obtained values were 1.3 mAbs and 5.1 mAbs.

In addition, the bilirubin binding capacities per mol of BSA were measured with respect to the obtained purified serum albumin, with use of a reagent for measuring bilirubin (manufactured by SEKISUI MEDICAL CO., LTD., "Autosera BIL-2", "Autosera D-BIL-2") by the azobilirubin method. The obtained values were 0.1 mmol and 0.5 mmol.

Hereinafter, the above purified serum albumin is also referred to as "purified BSA (1.3 mAbs/0.1 mmol)" and "purified BSA (5.1 mAbs/0.5 mmol)".

(2) Preparation of a Solution of Latex Having Treponema Pallidum Antigens Supported Thereon An amount of 400 µL of anti-treponema pallidum antigen solution dissolved in 100 mM phosphate buffer solution (pH 7.4) at a protein concentration of 150 µg/mL was added to 100 µL of polystyrene latex (solids content of 10 (w/v) %, manufactured by SEKISUI CHEMICAL Co., Ltd.) having the average particle size of 0.4 µm. The mixture was stirred at 4° C. for one hour.

Next, 2 mL of the purified BSA (5.1 mAbs/0.5 mmol) was added thereto and the mixture was stirred for one hour. The obtained liquid was centrifuged at 13000 rpm at 10° C. for 10 minutes. The obtained precipitation was added to 4 mL of a solution of the purified BSA (1.3 mAbs/0.1 mmol) and the latex was suspended. In this manner, the solution of latex having treponema pallidum antigens supported thereon was prepared.

Example 2

A solution of latex having treponema pallidum antigens supported thereon was prepared in the same manner as in Example 1, except the following. As a 2 M sodium chloride solution was mixed with the coupling agent in such a manner that the sodium chloride concentration was increased at the rate of 2 mM/min, the mixed solution was flowed at the rate of 10 mL/min. In this manner, a solution of purified BSA (0.9 mAbs/0.1 mmol) eluted within 87.7 to 88.9 minutes after commencement of mixing (fraction having a salt concentration of 98.4 to 100.8 mM) was obtained and was used as a blocking agent.

Example 3

A solution of latex having treponema pallidum antigens supported thereon was prepared in the same manner as in Example 1, except the following. As a 2 M sodium chloride solution was mixed with the coupling agent in such a manner that the sodium chloride concentration was increased at the rate of 2 mM/min, the mixed solution was flowed at the rate of 10 mL/min. In this manner, a solution of purified BSA (3.3 mAbs/0.3 mmol) eluted within 102.1 to 103.3 minutes after commencement of mixing (fraction having a salt concentration of 127.2 to 129.6 mM) was obtained and was used as a blocking agent.

Comparative Example 1

A solution of latex having treponema pallidum antigens supported thereon was prepared in the same manner as in Example 1, except that a solution of BSA was used without being purified by anion-exchange chromatography (hereinafter, referred to as crude BSA).

Here, 1% solution of the crude BSA had absorbance of light of 9.8 mAbs at a wavelength of 463 mm and the bilirubin binding capacity of 1.0 mmol per mol of BSA, which were measured in the same manner as in Example 1.

Comparative Example 2

A solution of latex having treponema pallidum antigens supported thereon was prepared in the same manner as in Example 1, except the following. As a 2 M sodium chloride solution was mixed with the coupling agent in such a manner that the sodium chloride concentration was increased at the rate of 2 mM/min, the mixed solution was flowed at the rate of 10 mL/min. In this manner, a solution of purified BSA (9.8 mAbs/1.0 mmol) eluted within 116.5 to 117.7 minutes after commencement of mixing (fraction having a salt concentration of 156.0 to 158.4 mM) was obtained and was used as a blocking agent.

Comparative Example 3

A solution of latex having treponema pallidum antigens supported thereon was prepared in the same manner as in Example 1, except the following. As a 2 M sodium chloride solution was mixed with the coupling agent in such a manner that the sodium chloride concentration was increased at the rate of 2 mM/min, the mixed solution was flowed at the rate of 10 mL/min. In this manner, a solution of purified BSA (17.9 mAbs/1.9 mmol) eluted within 130.9 to 132.1 minutes after commencement of mixing (fraction having a salt concentration of 184.8 to 187.2 mM) was obtained and was used as a blocking agent.

Comparative Example 4

A solution of latex having treponema pallidum antigens supported thereon was prepared in the same manner as in Example 1, except the following. As a 2 M sodium chloride solution was mixed with the coupling agent in such a manner that the sodium chloride concentration was increased at the rate of 2 mM/min, the mixed solution was flowed at the rate of 10 mL/min. In this manner, a solution of purified BSA (24.9 mAbs/2.6 mmol) eluted within 145.3 to 146.5 minutes after commencement of mixing (fractions having a salt concentration of 213.6 to 216.0 mM) was obtained and was used as a blocking agent.

(Evaluation)

The following evaluations were carried out by using the solutions of latex having treponema pallidum antigens supported thereon prepared in Examples 1 to 3 and Comparative Examples 1 to 4.

(1) Measurement of Standard Solution of Anti-Treponema Pallidum Antibodies

An amount of 15 μL of each standard syphilis positive serum (manufactured by SEKISUI MEDICAL Co., Ltd., 5 different concentrations) was mixed with 150 μL of a diluted sample fluid (100 mM phosphate buffer solution (pH 7.4) containing 1% of BSA and added with 0.2 (w/v) % of Lipidure (manufactured by NOF corporation)). Then, each mixed solution was held at 37° C. for a suitable time and was used as a standard solution of anti-treponema pallidum antibodies. The standard solution was added with 50 μL of a solution of latex having treponema pallidum antigens supported thereon and stirred. Then, the change of the absorbance of light between about 80 seconds and 300 seconds at wavelength of 700 nm was measured to obtain the absorbance change (Δ Abs).

Here, the measurement was carried out with use of Hitachi 7170 Auto Analyzer.

The results are shown in Table 1.

TABLE 1

| | | Blocking agent | | | | Latex suspension | | | | |
|---|---|---|---|---|---|---|---|---|---|---|
| | Lot No. of BSA | Anion-exchange chromatographic purification | Absorbance of light (A463 nm)/ 1% BSA | Bilirubin binding capacity/ BSA 1 mol | Sodium chloride concentration | anion-exchange chromatographic purification | Absorbance of light (A463 nm)/ 1% BSA | Bilirubin binding capacity/ BSA 1 mol | Sodium chloride concentration | Absorbance change at 127 T.U. |
| Comparative Example 1 | Lot 83 | No | 9.8 mAbs | 1.0 mmol | — | No | 9.8 mAbs | 1.0 mmol | — | 0.0212 |
| Example 1 | | Yes | 5.1 mAbs | 0.5 mmol | 69.6-72.0 mM | Yes | 1.3 mAbs | 0.1 mmol | 0-80 mM | 0.1239 |
| Example 2 | | | 0.9 mAbs | 0.1 mmol | 98.4-100.8 mM | | | | | 0.1029 |
| Example 3 | | | 3.3 mAbs | 0.3 mmol | 127.2-129.6 mM | | | | | 0.0988 |
| Comparative Example 2 | | | 9.8 mAbs | 1.0 mmol | 156.0-158.4 mM | | | | | 0.0593 |
| Comparative Example 3 | | | 17.9 mAbs | 1.9 mmol | 184.8-187.2 mM | | | | | 0.0348 |
| Comparative Example 4 | | | 24.9 mAbs | 2.6 mmol | 213.6-216.0 mM | | | | | 0.0188 |

(Abs)

(2) Measurement of Negative Samples

The absorbance changes (Δ Abs) were obtained in the same manner as in (1) except that saline and negative samples 1 to 10 were used as samples. Antibody titers were calculated from a calibration curve that is produced based on the measurement results of the standard. The results are shown in Table 2.

TABLE 2

| | Comparative Example 1 | Example 1 | Example 2 | Example 3 | Comparative Example 2 | Comparative Example 3 |
|---|---|---|---|---|---|---|
| Saline | 0 | 0 | 0 | 0 | 0 | 0 |
| Negative sample 1 | 4.4 | 1.3 | 1.4 | 0 | 0 | 17.5 |
| Negative sample 2 | 2.2 | 0 | 0 | 0 | 0 | 10.7 |
| Negative sample 3 | 11.0 | 0.6 | 3.2 | 3.1 | 3.7 | 40.7 |
| Negative sample 4 | 7.5 | 0 | 0 | 0 | 0.9 | 11.6 |
| Negative sample 5 | 5.0 | 0 | 0 | 0.1 | 1.5 | 20.0 |
| Negative sample 6 | 12.2 | 0.3 | 0.1 | 0 | 1.3 | 16.7 |

TABLE 2-continued

|  | Comparative Example 1 | Example 1 | Example 2 | Example 3 | Comparative Example 2 | Comparative Example 3 |
|---|---|---|---|---|---|---|
| Negative sample 7 | 7.5 | 0 | 0.2 | 3.5 | 0.8 | 0 |
| Negative sample 8 | 5.7 | 0 | 0 | 0 | 0.4 | 6.0 |
| Negative sample 9 | 9.1 | 0 | 0 | 0 | 2.6 | 9.8 |
| Negative sample 10 | 11.3 | 0 | 0 | 8.4 | 11.8 | 23.8 |

(T.U.)

Tables 1 and 2 clarify the following. When the solutions of latex having treponema pallidum antigens supported thereon prepared in Examples were used, reactivity was higher and less non-specific reactions occurred compared to the case where the latex solutions prepared in Comparative Examples were used.

Example 4

Three lots (Lot 83, Lot 91, Lot 77) of commercially-available bovine serum albumins were prepared. Solutions of latex having treponema pallidum antigens supported thereon were prepared in the same manner as in Example 1 by using the above three lots of bovine serum albumins.

Comparative Example 5

Solutions of latex having treponema pallidum antigens supported thereon were prepared in the same manner as in Comparative Example 1 except that three lots (Lot 83, Lot 91, Lot 77) of commercially-available bovine serum albumins were used without being purified.

(Evaluation)

Evaluation was carried out by using the solutions of latex having treponema pallidum antigens supported thereon prepared in Example 4 and Comparative Example 5 as follows.

An amount of 15 µL of each standard syphilis positive serum (manufactured by SEKISUI MEDICAL Co., Ltd., 5 concentrations) was mixed with 150 µL of a diluted sample fluid (100 mM phosphate buffer solution (pH 7.4) containing 1% of BSA and added with 0.2 (w/v) % of Lipidure (manufactured by NOF corporation)). Then, each mixed solution was held at 37° C. for a suitable time and was used as a standard solution of anti-treponema pallidum antibodies. The standard solution was added with 50 µL of a solution of latex having treponema pallidum antigens supported thereon and stirred. Then, the change of the absorbance of light between about 80 seconds and 300 seconds at wavelength of 700 nm was measured to obtain the absorbance change (Δ Abs).

Here, the measurement was carried out with use of Hitachi 7170 Auto Analyzer.

The results are shown in Table 3.

TABLE 3

|  |  | Blocking agent | | | Latex suspension | | | | |
|---|---|---|---|---|---|---|---|---|---|
|  | Lot No. of BSA | Anion-exchange chromatographic purification | Absorbance of light (A463 nm)/ 1% BSA | Bilirubin binding capacity/BSA 1 mol | Anion-exchange chromatographic purification | Absorbance of light (A463 nm)/ 1% BSA | Bilirubin binding capacity/BSA 1 mol | Absorbance change at 127 T.U. | Standard deviation |
| Example 4 | Lot 83 Lot 91 Lot 77 | Yes | 1.3 mAbs | 0.1 mmol | Yes | 1.3 mAbs | 0.1 mmol | 0.2230 0.2228 0.2075 | 0.0089 |
| Comparative Example 5 | Lot 83 Lot 91 Lot 77 | No | 9.8 mAbs | 1.0 mmol | No | 9.8 mAbs | 1.0 mmol | 0.0212 0.0709 0.0521 | 0.0250 |

(Abs)

Table 3 clarifies the following. When the solutions of latex having treponema pallidum antigens supported thereon prepared in Example were used, lot-to-lot difference of the serum albumins was smaller compared to the case where the latex solutions prepared in Comparative Example were used.

Example 5

A solution of latex having treponema pallidum antigens supported thereon was prepared in the same manner as in Example 1 except the following. A solution of the purified BSA (1.3 mAbs/0.1 mmol) obtained in Example 1 was concentrated and added to a commercially-available gel filtration column "Sephacryl S-200HR" (manufactured by GE Healthcare Inc.). The purified solution was further purified by gel filtration with use of 100 mM phosphate buffer solution (pH 7.4) and the BSA composed only of monomer fractions of the above purified solution was used.

Example 6

A solution of latex having treponema pallidum antigens supported thereon was prepared in the same manner as in Example 5 except the following. The BSA composed only of monomer fractions was used only as a blocking agent. The monomer fractions were obtained by further purifying the purified BSA solution (1.3 mAbs/0.1 mmol) obtained in Example 1 by gel filtration. The purified BSA solution (1.3 mAbs/0.1 mmol) obtained in Example 1 was used to prepare the solutions of latex having treponema pallidum antigens supported thereon.

Example 7

A solution of latex having treponema pallidum antigens supported thereon was prepared in the same manner as in Example 5 except the following. The BSA composed only of monomer fractions was used only as a blocking agent. The monomer fractions were obtained by further purifying the purified BSA solution (1.3 mAbs/0.1 mmol) obtained in Example 1 by gel filtration. A crude BSA solution was used to prepare the solutions of latex having treponema pallidum antigens supported thereon.
(Evaluation)

The following evaluations were carried out by using solutions of latex having treponema pallidum antigens supported thereon prepared in Examples 5 to 7.

An amount of 15 μL of each standard syphilis positive serum (manufactured by SEKISUI CHEMICAL Co., Ltd., 5 concentrations) was mixed with 150 μL of a diluted sample fluid (100 mM phosphate buffer solution (pH 7.4) containing 1% of BSA and added with 0.2 (w/v) % of Lipidure (manufactured by NOF corporation)). Then, each mixed solution was held at 37° C. for a suitable time and was used as a standard solution of anti-treponema pallidum antibodies. The standard solution was added with 50 μL of a solution of latex having treponema pallidum antigens supported thereon and stirred. Then, the change of the absorbance of light between about 80 seconds and 300 seconds at wavelength of 700 nm was measured to obtain the absorbance change (Δ Abs).

Here, the measurement was carried out with use of Hitachi 7170 Auto Analyzer.

The results are shown in Table 4.

Example 1 except that BSA solutions comprising mixed BSA materials at the ratios shown in Table 5 were used.

(Evaluation)

The following evaluations were carried out by using solutions of latex having treponema pallidum antigens supported thereon prepared in Reference. Examples 1 to 10.

An amount of 15 μL of each standard syphilis positive serum (manufactured by SEKISUI MEDICAL Co., Ltd., 5 concentrations) was mixed with 150 μL of a diluted sample fluid (100 mM phosphate buffer solution (pH 7.4) containing 1% of BSA and added with 0.2 (w/v) % of Lipidure (manufactured by NOF corporation)). Then, each mixed solution was held at 37° C. for a suitable time and was used as a standard solution of anti-treponema pallidum antibodies. The standard solution was added with 50 μL of a solution of latex having treponema pallidum antigens supported thereon and stirred. Then, the change of the absorbance of light between about 80 seconds and 300 seconds at wavelength of 700 nm was measured to obtain the absorbance change (Δ Abs).

TABLE 4

| | | Blocking agent | | | | Latex suspension | | | | |
|---|---|---|---|---|---|---|---|---|---|---|
| | Lot No. of BSA | Anion-exchange chromatographic purification | Absorbance of light (A463 nm)/ 1% BSA | Bilirubin binding capacity/ BSA 1 mol | Gel filtration purification | Anion-exchange chromatographic purification | Absorbance of light (A463 nm)/ 1% BSA | Bilirubin binding capacity/BSA 1 mol | Gel filtration purification | Absorbance change at 127 T.U. |
| Example 5 | Lot 83 | Yes | 1.3 mAbs | 0.1 mmol | Yes | Yes | 1.3 mAbs | 0.1 mmol | Yes | 0.2230 |
| Example 6 | | | | | | | | | No | 0.1841 |
| Example 7 | | | | | | No | 9.8 mAbs | 1.0 mmol | No | 0.1648 |

(Abs)

Table 4 clarifies that purification by gel filtration further improves reactivity.

Reference Examples 1 to 10

Solutions of latex having treponema pallidum antigens supported thereon were prepared in the same manner as in Here, the measurement was carried out with use of Hitachi 7170 Auto Analyzer.

The results are shown in Table 5.

In addition, FIG. 1 is a graph indicating the results shown in Table 5, in which added BSA rate is plotted on the vertical axis and absorbance change is plotted on the horizontal axis.

TABLE 5

| | | Blocking agent | | | | | Latex suspension | | |
|---|---|---|---|---|---|---|---|---|---|
| | | Purified BSA (3.3 mAbs/0.3 mmol) | | Added BSA | | | Absorbance of light | | Absorbance |
| | Lot No. of BSA | Proportion (wt %) | Sodium chloride concentration | Kind | Sodium chloride concentration | Proportion (wt %) | (A463 nm)/ 1% BSA | Bilirubin binding capacity/BSA 1 mol | change at 127 T.U. |
| Reference Example 1 | Lot 83 | 0 | 1.0-141.6 mM | 3.3 mAbs/ 0.3 mmol | 1.0-141.6 mM | 100 | 1.3 mAbs | 0.1 mmol | 0.1285 |
| Reference Example 2 | | 85 | | 11.4 mAbs/ 1.2 mmol | 141.6-170.4 mM | 15 | | | 0.1091 |

TABLE 5-continued

| | | Blocking agent | | | | Latex suspension | | |
| --- | --- | --- | --- | --- | --- | --- | --- | --- |
| | | Purified BSA (3.3 mAbs/0.3 mmol) | | Added BSA | | Absorbance of light | | Absorbance |
| | Lot No. of BSA | Proportion (wt %) | Sodium chloride concentration | Kind | Sodium chloride concentration | Proportion (wt %) | (A463 nm)/ 1% BSA | Bilirubin binding capacity/BSA 1 mol | change at 127 T.U. |
| Reference Example 3 | | 75 | | | | 25 | | | 0.0860 |
| Reference Example 4 | | 65 | | | | 35 | | | 0.0774 |
| Reference Example 5 | | 90 | | 17.5 mAbs/ 1.8 mmol | 170.4-199.2 mM | 10 | | | 0.0734 |
| Reference Example 6 | | 80 | | | | 20 | | | 0.0465 |
| Reference Example 7 | | 70 | | | | 30 | | | 0.0.354 |
| Reference Example 8 | | 95 | | 23.6 mAbs/ 2.5 mmol | 199.2-228.0 mM | 5 | | | 0.0632 |
| Reference Example 9 | | 85 | | | | 15 | | | 0.0281 |
| Reference Example 10 | | 75 | | | | 25 | | | 0.0162 |

(Abs)

INDUSTRIAL APPLICABILITY OF THE INVENTION

According to the present invention, it is possible to provide a purified serum albumin having less lot-to-lot variation; and an immunoassay method utilizing the purified serum albumin, in which high reactivity and less non-specific reactions are achieved.

BRIEF DESCRIPTION OF THE DRAWINGS

FIG. 1 is a graph indicating the results shown in Table 5, in which added BSA rate is plotted on the horizontal axis and absorbance change is plotted on the vertical axis.

The invention claimed is:

1. An immunoassay method comprising,
  mixing a biological sample with antigens or antibodies supported on an insoluble carrier to allow for an antibody-antigen reaction, and
  detecting agglutination,
  wherein a purified serum albumin is used as a blocking agent for the insoluble carrier having antigens or antibodies supported thereon, or in a suspension of the insoluble carrier having antigens or antibodies supported thereon, and
  wherein the purified serum albumin being composed mostly of a fraction having an absorbance of not exceeding 9.0 mAbs when measured in the form of a 1% by weight aqueous solution at a wavelength of 463 nm by using a quartz cell having an optical path length of 1.0 cm.

2. A reagent for preparation of solid-phase used in immunoassay, comprising a purified serum albumin comprising mostly a fraction,
  the fraction having an absorbance of not exceeding 9.0 mAbs when measured in the form of 1% by weight aqueous solution at a wavelength of 463 nm by using a quartz cell having an optical path length of 1.0 cm, and
  wherein the serum albumin is used as a blocking agent and/or in a suspension containing an insoluble carrier in an immunoassay method.

3. A purified serum albumin,
  wherein the purified serum albumin is used as a blocking agent and/or in a suspension containing an insoluble carrier in an immunoassay method, and
  is composed mostly of a fraction,
  the fraction having bilirubin binding capacity of not exceeding 0.9 mmol with respect to 1 mol of serum albumin.

4. An immunoassay reagent,
  which comprises a purified serum albumin mostly composed of a fraction,
  the fraction having bilirubin binding capacity of not exceeding 0.9 mmol with respect to 1 mol of serum albumin.

5. An immunoassay method comprising,
  mixing a biological sample with antigens or antibodies supported on an insoluble carrier to allow for an antibody-antigen reaction, and
  detecting agglutination, and
  wherein a purified serum albumin is used as a blocking agent for the insoluble carrier having antigens or antibodies supported thereon, or in a suspension of the insoluble carrier having antigens or antibodies supported thereon, and
  wherein the purified serum albumin being composed mostly of a fraction having bilirubin binding capacity of not exceeding 0.9 mmol with respect to 1 mol of serum albumin.

6. A reagent for preparation of solid-phase used in immunoassay comprising,
  a purified serum albumin comprising mostly a fraction,
  the fraction having bilirubin binding capacity of not exceeding 0.9 mmol with respect to 1 mol of serum albumin, and
  wherein the purified serum albumin is used as a blocking agent and/or in a suspension containing an insoluble carrier in an immunoassay method.

7. The immunoassay method according to claim 1, wherein the fraction of the purified serum albumin comprises bilirubin binding capacity of not exceeding 0.9 mmol with respect to 1 mol of serum albumin.

8. The immunoassay method according to claim 5, wherein the fraction of the purified serum albumin comprises an absorbance of not exceeding 9.0 mAbs when measured in the form of 1% by weight aqueous solution at a wavelength of 463 nm by using a quartz cell having an optical path length of 1.0 cm.

9. The immunoassay method of claim 1, wherein the purified serum albumin comprises additional fractions present in an amount from 0% by weight to 45% by weight.

* * * * *